(12) United States Patent
Hoppel et al.

(10) Patent No.: US 7,386,338 B2
(45) Date of Patent: Jun. 10, 2008

(54) BILATERAL IMAGING APPARATUS

(75) Inventors: Bernice E. Hoppel, Delafield, WI (US); LeRoy R. Blawat, Milwaukee, WI (US); John Lorbiecki, Hubertus, WI (US); Cynthia F. Maier, Wauwatosa, WI (US); Elisabeth Carol Angelos, Hartland, WI (US); Eddy Benjamin Boskamp, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 703 days.

(21) Appl. No.: 10/709,381

(22) Filed: Apr. 30, 2004

(65) Prior Publication Data

US 2005/0245805 A1    Nov. 3, 2005

(51) Int. Cl.
*A61B 5/055* (2006.01)
(52) U.S. Cl. ..................... 600/422; 324/318
(58) Field of Classification Search ............... 600/410, 600/422; 324/307, 309, 318, 322
See application file for complete search history.

(56) References Cited

U.S. PATENT DOCUMENTS

| | | | |
|---|---|---|---|
| 5,363,845 A | 11/1994 | Chowdhury et al. | |
| 5,706,812 A | 1/1998 | Strenk et al. | |
| 5,804,969 A * | 9/1998 | Lian et al. | 324/318 |
| 6,023,166 A * | 2/2000 | Eydelman | 324/318 |
| 6,163,717 A | 12/2000 | Su | 600/422 |
| 6,545,472 B2 | 4/2003 | Prussmann et al. | 324/307 |
| 6,889,073 B2 * | 5/2005 | Lampman et al. | 600/422 |
| 2004/0000907 A1 | 1/2004 | Ahluwalia et al. | 324/309 |

* cited by examiner

*Primary Examiner*—Ruth S Smith
(74) *Attorney, Agent, or Firm*—Cantor Colburn LLP

(57) ABSTRACT

An assembly of RF coils for bilateral imaging of a first and a second breast of the same person is disclosed. The assembly includes a first pair of coils having a first coil juxtaposed and underlapping a second coil, thereby defining juxtaposed edges of the first and second coils, and a second pair of coils having a third coil juxtaposed and underlapping a fourth coil, thereby defining juxtaposed edges of the third and fourth coils. The first coil has a first opening for receiving the first breast, the second coil has a second opening for receiving the second breast, the third coil substantially opposes the first coil, defining therebetween a first region for receiving the first breast, and the fourth coil substantially opposes the second coil, defining therebetween a second region for receiving the second breast.

25 Claims, 3 Drawing Sheets

BILATERAL IMAGING APPARATUS

BACKGROUND OF THE INVENTION

The present disclosure relates generally to an apparatus for bilateral imaging of a first and a second breast of a person, and particularly to an arrangement of RF coils for simultaneous bilateral imaging.

Magnetic resonance imaging (MRI) mammography is useful in assessing the size of a tumor for surgical planning, especially with difficult histology such as infiltrating lobular carcinomas and extensive intraductal components. It has also shown to be accurate in the staging of cancers as well as determining the amount of chest wall or pectoralis invasion. Screening of the opposite breast of interest may be important in cases where a patient has a form of disease with high probability of bilaterality, for example, invasive lobular carcinoma, as well as assessing patients for contralateral breast disease. Assessment of the contrast uptake dynamics through MR imaging has been found to increase specificity and change clinical treatment in many cases.

An MRI system uses a static magnetic field $B_0$ to align magnetic spins in the direction of the field, usually denoted along the z-axis. A rotating RF field $B_1$ applied perpendicular to the $B_0$ field will cause the spins to rotate into the transverse field at a resonant frequency. The transverse component of the magnetization can be detected through the use of an RF antenna or receiver coil, which is specifically tuned to the resonate frequency of the precessing spins, otherwise know as the Larmor frequency. The signal-to-noise-ratio (SNR) of the system is dependent on the filling factor of this RF coil, resulting in local RF coils being used to increase the SNR of the system. With RF coils, it is desirable to both optimize the SNR of the system and provide a comfortable environment for the patient, thus decreasing patient movement during the scan. It is also desirable to provide a coil that allows for optimal patient placement during the scan in order to minimize artifacts from the system.

With some MRI techniques, there may be trade-offs between spatial resolution and acquisition time, that is, using a low resolution imaging technique and acquiring many temporal time points versus using a mode of high resolution imaging and acquiring few temporal time points. For bilateral breast imaging acquisition, several methods have been used to produce dynamic enhancement parametric curves. The use of axial and coronal slices is commonly used but may reduce the acquisition efficiency and spatial resolution of the image. The axial volumes may be acquired with a significant amount of zero-filling in k-space in order to keep the acquisition times reasonable. However, for these interpolated data sets, the real spatial resolution of the images may not be equal to the reconstructed voxel size. A second imaging method is to toggle back and forth between the left and right breast volumes, thereby maintaining the spatial resolution but possibly effecting the temporal resolution and decreasing the efficacy of the enhancement curve. A third imaging method is to perform the imaging of the left and right breasts on separate days, which may be inconvenient for the patient.

An alternative imaging method is to use parallel imaging in the slice direction using a multi-element array coil where individual RF coil elements are more sensitive to one of the breast volumes than to the other. From the resultant data, a signal processing parallel imaging technique may be used to acquire sagittal slices from both breasts simultaneously. Here, a single large volume encompassing both left and right breasts is prescribed such that a volume V' is aliased back into a volume V. To unalias the volume data into slices corresponding to volumes V and V', the coil element sensitivities are used by the signal processing parallel imaging technique.

To advance the field of MRI mammography, there remains a need in the art to separate coil sensitivity maps in the encoding direction, thereby enabling higher temporal resolution and higher spatial resolution.

BRIEF DESCRIPTION OF THE INVENTION

Embodiments of the invention include an assembly of RF coils for bilateral imaging of a first and a second breast of the same person. The assembly includes a first pair of coils having a first coil juxtaposed and underlapping a second coil, thereby defining juxtaposed edges of the first and second coils, and a second pair of coils having a third coil juxtaposed and underlapping a fourth coil, thereby defining juxtaposed edges of the third and fourth coils. The first coil has a first opening for receiving the first breast, the second coil has a second opening for receiving the second breast, the third coil substantially opposes the first coil, defining therebetween a first region for receiving the first breast, and the fourth coil substantially opposes the second coil, defining therebetween a second region for receiving the second breast.

Other embodiments of the invention include an apparatus for bilateral imaging of a first and a second breast of the same person. The apparatus includes a first coil juxtaposed and underlapping a second coil by a first underlap dimension, and a third coil juxtaposed and underlapping a fourth coil by a second underlap dimension. The first coil has a first opening for receiving the first breast, the second coil has a second opening for receiving the second breast, the third coil substantially opposes the first coil, defining therebetween a first region for receiving the first breast, and the fourth coil substantially opposes the second coil, defining therebetween a second region for receiving the second breast. The second underlap dimension is equal to or greater than the first underlap dimension, the first coil has an inside diameter that is equal to or larger than the inside diameter of the third coil, and the second coil has an inside diameter that is equal to or larger than the inside diameter of the fourth coil.

Further embodiments of the invention include an apparatus for bilateral imaging of a first and a second breast of the same person. The apparatus includes a first set of coils with each coil of the first set of coils being underlapped with respect to each other coil of the first set of coils, and a second set of coils with each coil of the second set of coils being underlapped with respect to each other coil of the second set of coils. The second set of coils opposes the first set of coils, defining therebetween a first region and a second region for receiving the first and the second breast. Each coil in the first and the second sets of coils are configured to be operational independent of each of the aforementioned coils.

BRIEF DESCRIPTION OF THE DRAWINGS

Referring to the exemplary drawings wherein like elements are numbered alike in the accompanying Figures.

DETAILED DESCRIPTION OF THE INVENTION

An embodiment of the invention provides an arrangement of RF antennas or receiver coils that are configured in an underlapped arrangement for simultaneous acquisition of high-resolution sagittal images from both left and right breasts of a patient. The patient is placed relative to the coils in a prone position such that the breasts are directed downward under the influence of gravity into magnetization regions. While embodiments described and illustrated herein depict and describe RF coils having circular cross sections, it will be appreciated that the disclosed invention is also applicable to RF coils having other cross sectional geometries, such as rectangular for example.

Figure 1:
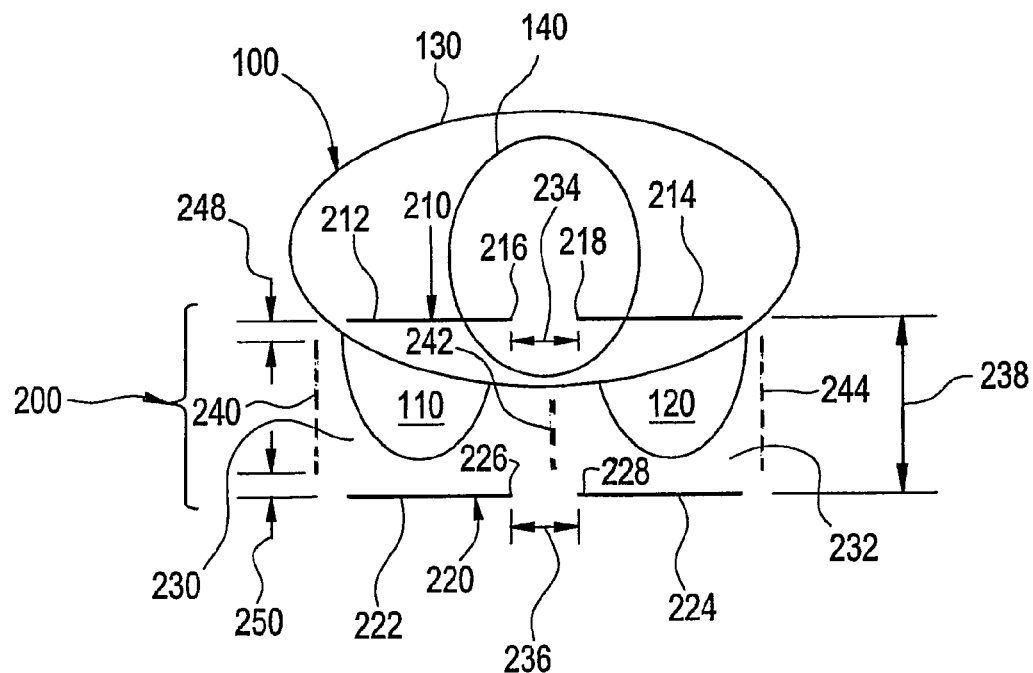
FIG. 1 depicts an exemplary coil arrangement in relation to a person placed in a prone position in accordance with embodiments of the invention.

FIG. 1 is an exemplary embodiment of a person 100 placed in a prone position relative to an assembly of RF coils 200 for bilateral imaging of a first and a second breast 110, 120, respectively, of person 100. In general, each coil of assembly 200 is depicted as a solid straight line, which represents the diameter, extending into and out of the plane of the paper, of the respective coil. Each coil has a central axis that is perpendicular to the respective solid straight line in a plane parallel to the plane of the paper. A first pair of coils 210 includes a first coil 212 juxtaposed and underlapping a second coil 214, thereby defining juxtaposed edges 216, 218 of coils 212, 214, respectively. While first and second coils 212, 214 are depicted intersecting the body 130 and head 140 of person 100, it will be appreciated that this is for illustrative purposes only, and as will be discussed in more detail later, an embodiment of the invention has first and second coils 212, 214 arranged within a bodyform 300, depicted in FIG. 2, that is contoured for a comfortable fit against the chest and torso of person 100. A second pair of coils 220 includes a third coil 222 juxtaposed and underlapping a fourth coil 224, thereby defining juxtaposed edges 226, 228 of coils 222, 224, respectively. Third coil 222 substantially opposes first coil 212, defining therebetween a first region 230 for receiving first breast 110. Fourth coil 224 substantially opposes second coil 214, defining therebetween a second region 232 for receiving second breast 120. As used herein, the term substantially opposes is intended to refer to two opposing coils that may be of slightly different size and therefore do not directly oppose each other at all points, but rather substantially oppose each other for purposes of image acquisition as herein disclosed.

The arrangement of first, second, third and fourth coils 212, 214, 222 and 224, may alternatively be viewed as having their respective central axes (not shown for clarity, but appreciated as being perpendicular to the solid lines illustrative of coils 212, 214, 222, 224) disposed substantially parallel to each other. However, since bodyform 300 may be contoured to fit person 100, first and second coils 212, 214 may have windings that are non-planar, thereby resulting in the central axes of first and second coils 212, 214 being skewed slightly with respect to the central axes of third and fourth coils 222, 224, respectively. Accordingly and as used herein, the term substantially parallel is intended to refer to two opposing coils being oriented somewhat facing each other while permitting some degree of skew between the axes of associated coils.

In an embodiment, juxtaposed edges 226, 228 of third and fourth coils 222, 224 oppose juxtaposed edges 216, 218 of first and second coils 212, 214, respectively. The distance between juxtaposed edges 216, 218 of first and second coils 212, 214 define a first underlap dimension 234, and the distance between juxtaposed edges 226, 228 of third and fourth coils 222, 224 define a second underlap dimension 236. In an embodiment, second underlap dimension 236 is equal to or greater than first underlap dimension 234. In an alternative embodiment, second underlap dimension 236 is about equal to first underlap dimension 234. First underlap dimension 234 is sized to provide a comfortable fit of bodyform 300 with respect to person 100, and with respect to the size of first and second breasts 110, 120 of person 100. In an exemplary embodiment, first underlap dimension 234 is equal to or greater than about 0.25-inches and equal to or less than about 2-inches. In another exemplary embodiment, first underlap dimension 234 is equal to or greater than about 1-inch and equal to or less than about 1.5-inches. In a further exemplary embodiment, first underlap dimension is equal to about 1.25-inches.

A single bodyform 300 may be configured with a fixed first underlap dimension 234 to accommodate the majority of persons 100 comfortably, multiple bodyforms 300 may be configured with different first underlap dimensions 234 to more comfortably accommodate a wider range of persons 100 having different sizes of first and second breasts 110, 120, or bodyform 300 may be configured having an adjustable first underlap dimension 234 that is sized according to the size of person 100 scheduled for an MRI.

Figure 2:
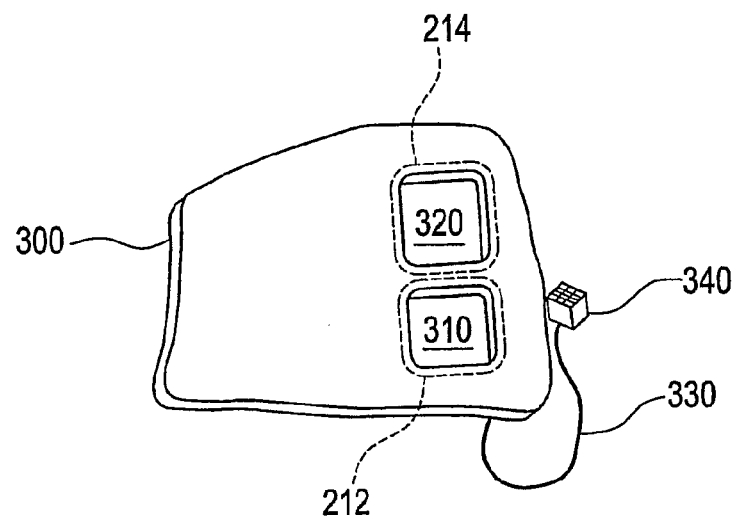
FIG. 2 depicts a portion of the coil arrangement of FIG. 1 for use in accordance with embodiments of the invention.

Referring to FIG. 2, an embodiment of bodyform 300 includes first coil 212 and second coil 214 encapsulated within semi-rigid foam that makes up bodyform 300. Central to first and second coils 212, 214 within bodyform 300 are first and second openings 310, 320 for receiving first and second breasts 110, 120, respectively. Connected to first and second coils 212, 214 is a signal wire 330 with a connector 340 and an end thereof for providing signal communication to and from first and second coils 212, 214 and a control station (not shown). In an embodiment, first coil 212 has an inside diameter that is equal to or larger than the inside diameter of third coil 222, and second coil 214 has an inside diameter that is equal to or larger than the inside diameter of fourth coil 224. In an exemplary embodiment, first and second coils 212, 214 have an inside diameter equal to or greater than about 6.75-inches, and third and fourth coils 222, 224 have an inside diameter equal to or greater than about 6.25-inches. In another exemplary embodiment, first and second coils 212, 214 have an inside diameter equal to about 7.75-inches, and third and fourth coils have an inside diameter equal to about 7.25-inches. While reference is made herein to inside diameters of coils 212, 214, 222, 224, it will be appreciated by reference to first and second openings 310, 320 of FIG. 2 that coils 212, 214, 222, 224 may be rectangular in shape, and that the aforementioned inside diameters may be replaced by major and minor dimensions of openings 310, 320. Accordingly and as used herein, the term inside diameter is intended to also refer to the maximum inside diameter that would fit within the major and minor dimensions of opening 310, 320.

Figure 3:
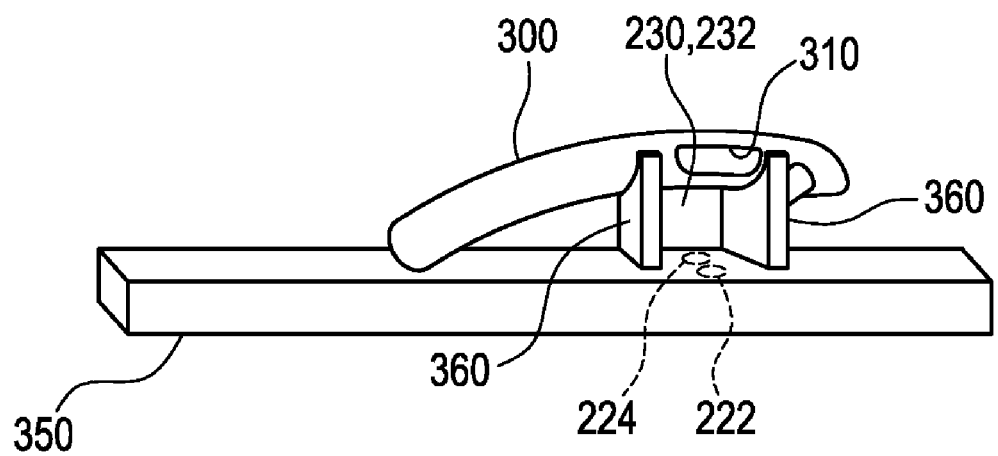
FIG. 3 depicts an isometric view of the coil arrangement of FIG. 1 including the portion of FIG. 2.

Referring to FIG. 3, an embodiment of bodyform 300 is placed on a table 350 via supports 360, and third and fourth coils 222, 224 are disposed within table 350. The height of supports 360 may either be fixed to accommodate the majority of sizes of person 100, or adjustable, thereby enabling adjustment of the distance 238 between first and second pairs of coils 210, 220 to accommodate a wider range of sizes of person 100. With person 100 lying on bodyform 300, first and second breasts 110, 120, under the influence of gravity, extend through first and second openings 310, 320 of first and second coils 212, 214 toward third and fourth coils 222, 224, but do not extend beyond third and fourth coils 222, 224. As seen in FIG. 3, side access between supports 360 may be provided, thereby providing an open region between first and second pairs of coils 210, 220 for access to first and second regions 230, 232 for an interventional procedure, such as a biopsy for example.

In an alternative embodiment, and referring now back to FIG. 1, a fifth, sixth, and seventh coil 240, 242, 244, respectively, may be placed between first and second pairs of coils 210, 220 and arranged with their central axes substantially perpendicular to the axes of first, second, third and fourth coils 212, 214, 222, 224. Fifth coil 240 is disposed superior to (that is, to the outer side of) first region 230, sixth coil 242 is disposed inferior to (that is, to the inner sides of) first and second regions 230, 232, and seventh coil is disposed superior to second region 232. Fifth coil 240 is underlapped with respect to first and third coils 212, 222, as shown by dimensions 248, 250, respectively. Dimension 248 is alternatively referred to as the underlap dimension at the posterior edge of fifth coil 240, and dimension 250 is alternatively referred to as the underlap dimension at the anterior edge of fifth coil 240. Accordingly, the outer diameter of fifth coil 240 does not overlap the axial length of either first coil 212 or third coil 222. Similar to the underlapping arrangement of fifth coil 240, seventh coil 244 is disposed underlapped with respect to second and fourth coils 214, 224, and sixth coil 242 is disposed underlapped with respect to both first and third coils 212, 222, and second and fourth coils 214, 224. The underlapping dimensions associated with seventh coil 244 are not shown for clarity but are similar to those illustrated by underlapping dimensions 248, 250. The underlapping dimension associated with the anterior edge of sixth coil 242 may be the same as underlapping dimension 250, but the underlapping dimension associated with the posterior edge of sixth coil 242 may be greater than the underlapping dimension 248 in order to comfortably accommodate the sternum of person 100.

Each of the seven coils 212, 214, 222, 224, 240, 242, 244 may be configured to be operational independent of each other, thereby providing for a high degree of control over the amount of magnetization person 100 is exposed to. For example, a person 100 having small breasts 110, 120 may undergo an MRI procedure where only first and second coils 212, 214 are energized, while a person 100 having large breasts 110, 120 may undergo an MRI procedure where first, second, third and fourth coils 212, 214, 222, 224 are energized. For greater sensitivity, fifth, sixth and seventh coils 240, 242, 244 may be energized. For a person 100 requiring an MRI procedure on only one breast, only one set of coils for that breast may be energized. The control signals for energizing or not energizing a particular coil may be provided via signal wire 330 and connector 340 from the control station.

Figure 4:
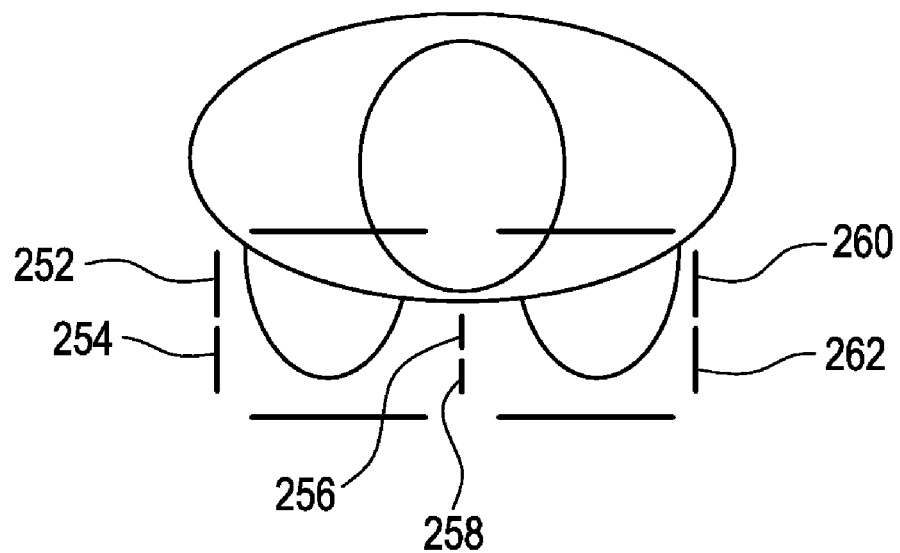
FIG. 4 depicts an alternative coil arrangement to that of FIG. 1.

In an alternative embodiment, and now referring to FIG. 4, fifth, sixth and seventh coils 240, 242, 244 may be bifurcated into multiple coils 252, 254, 256, 258, 260, 262 along the anterior-posterior direction. Similarly, third and fourth coils 222, 224 may be bifurcated into multiple coils (not shown) and placed in the superior-inferior direction along each breast 110, 120 for use with both phase and slice parallel imaging simultaneously. The use of bifurcated fifth, sixth and seventh coils 240, 242, 244 may be advantageous when working in the axial plane with the slice encoded in the superior/inferior direction.

Parallel imaging in the slice direction using embodiments of the invention herein disclosed allows simultaneous acquisition of high-resolution sagittal images from both left and right breasts with good fat suppression. Each line of data is acquired from the left and right breasts simultaneously, with only minimal increase of acquisition time relative to a unilateral exam with equal spatial resolution. Embodiments of the invention using underlapped coils as herein disclosed eliminate the hot spots or bright spots commonly seen in breast imaging or fat saturated imaging in the region where coils typically overlap. Also, by using underlapped coils as herein disclosed, it is easier to separate the coil sensitivity maps in the encoding direction, thereby enabling higher temporal resolution and higher spatial resolution in the absence of signal processing parallel imaging techniques that act on the data subsequent to encoding, which in turn provides for a greater signal-to-noise ratio (SNR), greater image quality, and lower acquisition time.

Figure 5:
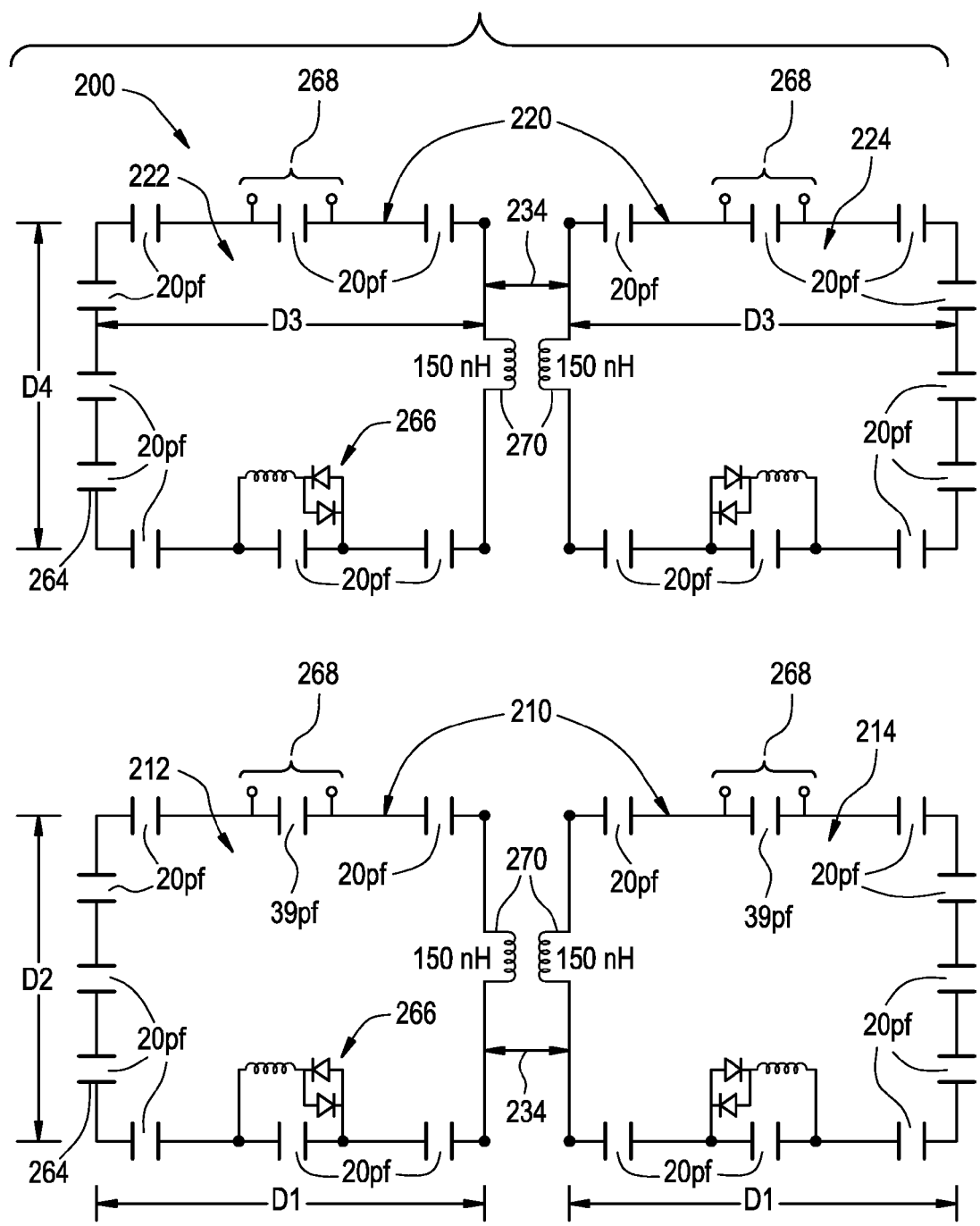
FIG. 5 depicts an exemplary embodiment of a four-channel coil arrangement similar to that of FIG. 1.

Referring now to FIG. 5, an exemplary embodiment of a four-channel breast coil assembly 200 is depicted in schematic format. First pair of coils 210, also referred to as posterior coils, have loop dimensions of D1 by D2, and second pair of coils 220, also referred to as anterior coils, have loop dimensions of D3 by D4. In an embodiment, D1 is 7.25-inches, D2 is 6.75-inches, D3 is 7.75-inches, and D4 is 6.75-inches (these dimensions may be variable). First and second coils 212, 214 are constructed similarly, and third and fourth coils 222, 224 are constructed similarly. First and second coils 212, 214, and third and fourth coils 222, 224, are each separated by dimension 234, which in an embodiment is 1.25-inches. While dimension 234 is shown to be the same for first and second pairs of coils, 210, 220, the use of identical dimensions is not a necessary requirement of the invention.

In the embodiment of FIG. 5, the schematics of coils 212, 214, 222, are 224 are shown to be similarly arranged with a plurality of serially connected capacitors 264, having a value of 20-picofarads (pF) for example, a passive decoupling circuit 266 on the inferior end, and an active decoupling circuit 268 on the superior end input ports. An embodiment of the invention uses two inductors 270 wound in opposite directions to cancel out mutual inductance between the coils in the left/right direction. However, alternative embodiments may use other means for canceling out the mutual inductance between the left/right coils.

In an embodiment, passive decoupling circuit 266 includes the combination of an inductor and two back-to-back diodes in parallel with capacitor 264, and active decoupling circuit 268 includes a balun, which may be a wire-wound transformer or any other type of balun suitable for the purpose of decoupling as herein disclosed. For example, cable trap baluns may be applied at the input ports of each coil to minimize standing waves that propagate on the shield of a connected coax cable (not shown). In first coil pair 210, active decoupling circuit 268 includes a 39 pF capacitor, while in second coil pair 220, active decoupling circuit 268 includes a 20 pF capacitor, however, other capacitor values may be employed as suitable.

In the anterior-posterior direction, first and second pairs of coils 210, 220 are decoupled by means of distance 238 (see FIG. 1), which has been found to be suitable for a loaded coil Q-factor of 20 and an unloaded coil Q-factor of 140. In an exemplary embodiment using pre-amplifier decoupling on the breast coils, it was found that first and second pairs of coils 210, 220 demonstrated little coupling at an average frequency of about 126.8 Mega-Hertz (MHz) over a separation distance 238 of about 4-inches to about 7-inches. An embodiment of the invention uses a pre-amplifier decoupling having an impedance of 800 ohms.

As disclosed, some embodiments of the invention may include some of the following advantages: a reduction in the magnitude and intensity of hot spots in the resulting image as a result of the underlapped arrangement of coils; an increase in temporal resolution with the use of the slice parallel imaging technique; the ability to energize and use any of the coils in the assembly individually or in any combination; increased speed of imaging as a result of coil placement that provides for parallel imaging with optimized image volume; the ability to switch between upper coils, lower coils, right coils, left coils, or all coils, for use with both unilateral and bilateral imaging; the ability to use upper coils and lower coils separately for maximum signal-to-noise ratio with small breasted or large breasted patients; an arrangement of MRI coils that are laterally open to allow for breast biopsy; and an arrangement of MRI coils that are sized to give sensitivity in the chest wall and armpit areas.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

The invention claimed is:

1. An assembly of RF coils for bilateral imaging of a first and a second breast of the same person, the assembly comprising:
    a first pair of coils comprising a first coil juxtaposed and underlapping a second coil, thereby defining juxtaposed edges of the first and second coils;
    a second pair of coils comprising a third coil juxtaposed and underlapping a fourth coil, thereby defining juxtaposed edges of the third and fourth coils;
    the first coil having a first opening for receiving the first breast;
    the second coil having a second opening for receiving the second breast;
    the third coil substantially opposing the first coil, defining therebetween a first region for receiving the first breast; and
    the fourth coil substantially opposing the second coil, defining therebetween a second region for receiving the second breast;
    wherein the first pair of coils is configured to be operational in the absence of the second pair of coils being operational.

2. The assembly of claim 1, wherein:
    the juxtaposed edges of the first and second coils oppose the juxtaposed edges of the third and fourth coils, respectively.

3. The assembly of claim 1, wherein:
    the distance between the juxtaposed edges of the first and second coils define a first underlap dimension; and
    the distance between the juxtaposed edges of the third and fourth coils define a second underlap dimension, the second underlap dimension being equal to or greater than the first underlap dimension.

4. The assembly of claim 3, wherein:
    the second underlap dimension is about equal to the first underlap dimension.

5. The assembly of claim 3, wherein:
    the first underlap dimension is equal to or greater than about 0.25-inches and equal to or less than about 2-inches.

6. The assembly of claim 5, wherein:
    the first underlap dimension is equal to or greater than about 1-inch and equal to or less than about 1.5-inches.

7. The assembly of claim 6, wherein:
    the first underlap dimension is equal to about 1.25-inches.

8. The assembly of claim 1, wherein:
    the axis of the third coil is disposed substantially parallel to the axis of the first coil; and
    the axis of the fourth coil is disposed substantially parallel to the axis of the second coil.

9. The assembly of claim 1, wherein:
    the first coil has an inside diameter that is equal to or larger than the inside diameter of the third coil; and
    the second coil has an inside diameter that is equal to or larger than the inside diameter of the fourth coil.

10. The assembly of claim 9, wherein:
    the first and second coils have an inside diameter equal to or greater than about 6.75-inches; and
    the third and fourth coils have an inside diameter equal to or greater than about 6.25-inches.

11. The assembly of claim 10, wherein:
    the first and second coils have an inside diameter equal to about 7.75-inches; and
    the third and fourth coils have an inside diameter equal about 7.25-inches.

12. The assembly of claim 1, wherein:
    the first pair of coils have windings that are non-planar.

13. The assembly of claim 1, wherein:
    the third and fourth coils oppose the first and second coils, respectively, by a defined distance such that the first and second breasts, under the influence of gravity, extend through the first and second openings of the first and second coils toward the third and fourth coils without extending beyond the third and fourth coils.

14. The assembly of claim 13, wherein:
    the defined distance is adjustable.

15. The assembly of claim 1, wherein:
    the first, second, third and fourth coils are each configured to be operational independent of each other.

16. The assembly of claim 1, further comprising:
    a fifth, a sixth and a seventh coil, each having axes arranged substantially perpendicular to the axes of the first, second, third and fourth coils;
    wherein the fifth coil is disposed superior to the first region, the sixth coil is disposed inferior to the first and second regions, and the seventh coil is disposed superior to the second region.

17. The assembly of claim 16, wherein:
    the fifth and sixth coils are each disposed underlapped with respect to the first and third coils; and
    the sixth and seventh coils are each disposed underlapped with respect to the second and fourth coils.

18. The assembly of claim 17, further comprising:
an eighth coil oriented similar to and proximate the sixth coil, the sixth coil disposed proximate the first region, the eighth coil disposed proximate the second region;
wherein the eighth coil is disposed underlapped with respect to the second and fourth coils.

19. The assembly of claim 1, further comprising:
an open region between the first and second pairs of coils to allow access therebetween to the first and second regions.

20. An apparatus for bilateral imaging of a first and a second breast of the same person, the apparatus comprising:
a first coil juxtaposed and underlapping a second coil by a first underlap dimension;
a third coil juxtaposed and underlapping a fourth coil by a second underlap dimension;
the first coil having a first opening for receiving the first breast;
the second coil having a second opening for receiving the second breast;
the third coil substantially opposing the first coil, defining therebetween a first region for receiving the first breast; and
the fourth coil substantially opposing the second coil, defining therebetween a second region for receiving the second breast;
wherein the second underlap dimension is equal to or greater than the first underlap dimension;
wherein the first coil has an inside diameter that is equal to or larger than the inside diameter of the third coil; and
wherein the second coil has an inside diameter that is equal to or larger than the inside diameter of the fourth coil;
wherein the first and second coils are configured to be operational independent of the third and fourth coils.

21. The apparatus of claim 20, wherein the third and fourth coils oppose the first and second coils, respectively, by a defined distance such that the first and second breasts, under the influence of gravity, extend through the first and second openings of the first and second coils toward the third and fourth coils without extending beyond the third and fourth coils.

22. The apparatus of claim 21, wherein:
the first, second, third and fourth coils are each configured to be operational independent of each other.

23. The apparatus of claim 22, further comprising:
a fifth, a sixth and a seventh coil, each having axes arranged substantially perpendicular to the axes of the first, second, third and fourth coils;
wherein the fifth coil is disposed superior to the first region, the sixth coil is disposed inferior to the first and second regions, and the seventh coil is disposed superior to the second region;
the fifth and sixth coils are each disposed underlapped with respect to the first and third coils; and
the sixth and seventh coils are each disposed underlapped with respect to the second and fourth coils.

24. An apparatus for bilateral imaging of a first and a second breast of the same person, the apparatus comprising:
a first set of coils with each coil of the first set of coils being underlapped with respect to each other coil of the first set of coils;
a second set of coils with each coil of the second set of coils being underlapped with respect to each other coil of the second set of coils; and
the second set of coils opposing the first set of coils, defining therebetween a first region and a second region for receiving the first and the second breast;
wherein each coil in the first and the second sets of coils are configured to be operational independent of each of the aforementioned coils.

25. The apparatus of claim 24, further comprising:
an open region between the first and second sets of coils to allow access therebetween to the first and second regions.

\* \* \* \* \*